US012611159B2

(12) United States Patent (10) Patent No.: US 12,611,159 B2
Zaboronok et al. (45) Date of Patent: Apr. 28, 2026

(54) DIGITAL STETHOSCOPE

(71) Applicant: OBSHCHESTVO S OGRANICHENNOY OTVETSTVENNOST'YU "MEDHARD", Moscow (RU)

(72) Inventors: Anatoli Petrovich Zaboronok, Minsk (BY); Maksim Grigorievich Humeniuk, Moscow (RU)

(73) Assignee: OBSHCHESTVO S OGRANICHENNOY OTVETSTVENNOST'YU "MEDHARD", Moscow (RU)

( * ) Notice: Subject to any disclaimer, the term of this patent is extended or adjusted under 35 U.S.C. 154(b) by 455 days.

(21) Appl. No.: 18/265,823

(22) PCT Filed: Nov. 26, 2021

(86) PCT No.: PCT/RU2021/050394
§ 371 (c)(1),
(2) Date: Jun. 7, 2023

(87) PCT Pub. No.: WO2022/124940
PCT Pub. Date: Jun. 16, 2022

(65) Prior Publication Data
US 2024/0032887 A1 Feb. 1, 2024

(30) Foreign Application Priority Data

Dec. 7, 2020 (RU) ................................ 2020140165

(51) Int. Cl.
A61B 7/04 (2006.01)
G16H 50/20 (2018.01)
(Continued)

(52) U.S. Cl.
CPC ............... A61B 7/04 (2013.01); G16H 50/20 (2018.01); G16H 80/00 (2018.01); H04R 1/46 (2013.01)

(58) Field of Classification Search
CPC .. A61B 7/02; A61B 7/026; A61B 7/04; G16H 50/20; G16H 80/00; G16H 40/67; H04R 1/46
(Continued)

(56) References Cited

U.S. PATENT DOCUMENTS 7,774,852 B2 * 8/2010 Yokota ................... G16H 10/60
726/28
9,265,478 B2 * 2/2016 Wang ....................... A61B 7/04
(Continued)

FOREIGN PATENT DOCUMENTS

CN 201939499 U 8/2011
CN 202365802 U 8/2012
(Continued)

*Primary Examiner* — Xu Mei
(74) *Attorney, Agent, or Firm* — Boyle Fredrickson, S.C.

(57) ABSTRACT
An auscultation device that can be used for telemedicine consultations and real-time telemedicine monitoring. The digital stethoscope includes a detector of analog acoustic signals from the patient and a data processing system implemented via a secure encrypted web-protocol and accessible via the user interface of a progressive web-application on a portable computing device of the patient/ physician with connected headphones. The acoustic signal detection device comprises a sequentially connected audio microphone, an analog signal pre-amplifier, an ADC, a microcontroller, and a battery. The microcontroller combines the signals from the ADC and the device status signals into a single packet and transmits it wirelessly to the data processing system. The software processing is carried out on the physician's or patient's device. An increase in the quality/speed of signal processing is achieved with reduced
(Continued)

power consumption and with the possibility of safe auscultation of patients with highly contagious diseases, e.g., COVID-19.

15 Claims, 8 Drawing Sheets

(51) Int. Cl.
    *G16H 80/00*       (2018.01)
    *H04R 1/46*       (2006.01)

(58) Field of Classification Search
    USPC .................... 381/67; 181/131, 137; 128/715;
                                           600/528, 586
    See application file for complete search history.

(56) References Cited

U.S. PATENT DOCUMENTS

| | | | | |
|---|---|---|---|---|
| 10,265,043 B2 * | 4/2019 | Hussain | ................... | A61B 7/04 |
| 11,026,654 B2 * | 6/2021 | Friedman | ................. | A61B 7/04 |
| 12,249,419 B2 * | 3/2025 | Blair | ........................ | A61B 7/04 |
| 2007/0098187 A1 | 5/2007 | Lee et al. | | |
| 2008/0077435 A1 * | 3/2008 | Muradia | ................ | G16H 40/67 |
| | | | | 705/2 |
| 2014/0018779 A1 * | 1/2014 | Worrell | .................. | G16H 40/67 |
| | | | | 606/1 |
| 2015/0148707 A1 * | 5/2015 | Bedingham | .............. | A61B 7/04 |
| | | | | 600/586 |
| 2023/0270389 A1 * | 8/2023 | Randall | ................ | A61B 5/0022 |
| | | | | 600/586 |

FOREIGN PATENT DOCUMENTS

| | | | | | |
|---|---|---|---|---|---|
| CN | 204890029 U | 12/2015 | | | |
| CN | 111820937 A | 10/2020 | | | |
| KR | 20150001009 A | 1/2015 | | | |
| TW | 201735016 A | 10/2017 | | | |
| WO | WO-0224074 A1 * | 3/2002 | .............. | A61B 7/04 |
| WO | 2008097008 A1 | 8/2008 | | | |

* cited by examiner

DIGITAL STETHOSCOPE

FIELD OF THE INVENTION

The invention relates to medical electronic devices, in particular, to devices for auscultation—a physical method of medical diagnosis, consisting in listening to and analyzing sounds formed as a result of functioning of the internal organs of a human or an animal. The device can be used for telemedicine consultations and real-time telemedicine monitoring, regardless of the distance between the patient and the physician.

BACKGROUND OF THE INVENTION

Mechanical stethoscopes have been developed to detect sounds produced by the body, such as heart and lung sounds. A stethoscope is a basic tool used in the diagnosis of diseases and conditions of the cardiovascular system. It serves as the most commonly used method for the diagnosis of such diseases and conditions in primary health care and in circumstances where comprehensive medical equipment is not available, for example, in remote areas.

Physicians appreciate the possibility of making a diagnosis based on sounds heard through a stethoscope. This skill is acquired and improved throughout years of practice. The acoustic detection of abnormal cardiac activity is complicated by the fact that heart tones are often separated from each other by very short periods, and that signals characterizing cardiac disorders are often less audible than normal heart sounds. Physicians often spend a lot of time memorizing the characteristics of normal and abnormal body sounds, such as the sounds of the heart and lungs heard with their specific stethoscope. For example, heart murmurs are classified based on the typical loudness of the sounds.

Modern digital stethoscopes may save the information obtained during an examination and transfer it to a personal computer (PC) for retrospective analysis. Such devices require a sufficiently high qualification of healthcare professionals for accurate interpretation of the results obtained and are used mainly in in-person contact of a physician/ assistant physician with a patient in inpatient and outpatient settings. Digital stethoscopes are described in WO2013086112 A1, WO2002032313 A2, U.S. Pat. No. 6,544,198 B2, RU196687 U1, KR20110041455 A, KR20130022141 A.

The closest analog to the claimed invention is the auscultation system disclosed in the international application WO2013086112 A1 (3M™ Littmann® electronic stethoscope, models 3100, 3200). This system includes a local part and a remote part. The local part comprises a sensor, an analog processing circuit for pre-filtering and amplifying the signals generated by the sensor, a power supply, a user interface, a configuration manager and the first communication module. The remote part comprises a digital filter including a microprocessor configured to apply digital filtering of processed signals, a power supply, and a second communication module. Communication modules can include wireless transceivers for receiving and transmitting data over a wireless connection. In the embodiment for telemedicine, a wireless headset for measuring a signal from a person transmits the processed signal to wireless headphones via Bluetooth.

The drawback of this solution and the prior art in general is the use of hardware filters (e.g., a band pass filter based on resistors and capacitors) and microcontrollers to filter analog signals of sound synthesis from a digital stream and to apply digital signals to the audio signal. In microcontrollers that synthesize sound and apply filters, the algorithms that produce this action have strict preset parameters, which significantly complicates the updating of these algorithms (in some devices this is not even provided). The digital filters built into the microcontrollers are preset versions of equalizers that cannot be changed based on the preferences of a clinical practitioner. These digital filters in their closest analog serve for psychoacoustic imitation of the operation of mechanical stethoscopes of the company's product line. This significantly increases the cost of the device, and also makes it extremely difficult to implement improved sound processing algorithms.

Moreover, in the closest analog and in existing solutions, the recording and preservation of the audio signal occurs after applying digital filters to the received sound, which makes it difficult for another specialist to analyze sounds, since different physician may have different psychoacoustic perception of sounds, and the specialist who recorded the sound could apply the wrong digital filter. It should be noted that the duration of the audio signal recording in the stethoscope considered the closest analog, is limited in its duration in seconds and the number of records saved in the stethoscope memory. It makes it difficult to save information about rare diagnostic signals (rare extra heart beats, adventitious breath sounds etc.).

Thus, the technical problem of prior art is the lack of simple devices in which 1) signal processing is carried out outside the hardware of the device, which allows you to use a stethoscope with one or more wireless headsets simultaneously in real time on one or more user devices,
2) there is real-time visualization of the received audio signal, which is an important component of the diagnostic process when the physician perceives the information received,
3) there is a possibility of using a neural network as a physician's assistant when working with data obtained from a stethoscope, there is a possibility of real-time audio-visual contact between the physician and the patient.
4) there is a possibility of consulting patients with highly contagious diseases (e.g. COVID-19). In existing auscultation solutions, the physician has to break the integrity of personal protective equipment in order to insert the stethoscope tubes into his/her ears.

Therefore, there is a need to develop a new digital stethoscope that will solve all the above mentioned problems.

SUMMARY OF THE INVENTION

The technical problem solved by the invention is the development of a simple easy-to-use universal digital stethoscope that would eliminate all existing problems of similar devices and would allow analyzing and interpreting the signal by a physician and/or artificial intelligence in real time with high quality and speed of signal processing.

The technical result achieved by using the invention is to improve the quality and speed of signal processing, the possibility of analyzing and interpreting the signal by a physician and/or artificial intelligence in real time.

An additional technical result consists in a reduction in power consumption.

The technical result is provided by the digital stethoscope including a device for detecting analog acoustic signals from the patient and at least one data processing system implemented through a secure encrypted web protocol and accessible through the user interface of a progressive web application on at least one portable computing device of the patient and/or physician with connected software at least with one pair of headphones, wherein the device for detecting analog acoustic signals from the patient comprises a sequentially connected audio microphone, an analog signal pre-amplifier, an ADC, a microcontroller, and a battery; the microcontroller is configured to combine signals from the ADC and device status signals into a single digital packet and transmit a packet containing digital data via a wireless data transmission channel to the system data processing; and at least one data processing system is configured to receive the specified digital packet and to perform its software processing in real time in a progressive web application running on the device of the physician and/or patient, wherein the progressive web application is configured to execute the following commands:

obtaining patient information and storing data in a data storage;
    processing of the received digital data packet with subsequent conversion of data from the packet into an audio signal and into device status data for detecting analog acoustic signals,
    saving device status data and recording audio signal to the data storage,
    displaying the audio signal in real time as an audiogram in the physician's web browser window,
    processing of the audio signal based on user settings, including the application of software noise reduction algorithms to the audio signal, software application of at least one digital filter on the audio signal,
    output of the processed audio signal in real time via the audio channel of the patient's and/or physician's portable computing device to at least one pair of headphones,
    storing data on applied digital filters to the audio signal and data on analysis performed by a physician and/or a neural network in the data storage.

In some embodiments of the invention, a device for detecting analog acoustic signals from a patient additionally comprises at least one LED and an element to turn on/off the device that is connected to a microcontroller, wherein the microcontroller is configured to supply a control signal to at least one LED to turn it on in the event of a decrease in battery charge and/or in the case of switching the device on and/or off. The signals about the device status are the signals selected from a group consisting of: information about the battery charge, information about turning on the device, information about the degree of amplification of the analog signal received from the analog signal pre-amplifier.

In some embodiments of the invention, the software interface of a progressive web application provides a variety of interface calls selected from a group consisting of: an interface for personal use, an interface for in-person auscultation, a patient interface for telemedicine consultation, a physician interface for telemedicine consultation.

In some embodiments for telemedicine consultation, it includes two portable computing devices, one of which belongs to the patient, and the other one to the physician, wherein the data processing system, accessible through the user interface of a progressive web application in a web browser on a patient's portable computing device is configured to receive a digital data packet from a device for detecting analog acoustic signals via a telecommunications channel, while the data processing system accessible through the user interface of a progressive web-application in a web-browser on the physician's portable computing device is configured to receive a digital data packet from the patient's data processing system and its software processing in real time.

In some embodiments, the connection between the patient's web browser and the physician's web browser is established via the WebRTC protocol, within which the browsers exchange audio, video and digital data.

In some embodiments, the user interface of a progressive web application is configured to allow the user to select modes selected from a group consisting of: a mode for receiving input from a patient or a physician, an audio recording mode, an audio display mode in the form of an audiogram and applying at least one digital filter to it, a recording mode for analyzing the processed audio signal.

In some embodiments, at least one portable computing device of the physician and/or patient is selected from a group consisting of: smartphone, personal computer, tablet.

In some embodiments, the data storage is cloud-based and/or local.

In some embodiments, the data storage is public and/or private and/or hybrid.

In some embodiments, the data storage is configured to be copied to a remote telemedicine web server to ensure synchronization between portable computing devices of the patient and/or the physician via the Internet, providing access to physicians or neural networks for retrospective analysis of stored records, as well as for training a neural network that can be used by a physician as an online assistant during the auscultation.

In some embodiments, the wireless channel for transmitting a digital data packet operates according to a standard selected from a group consisting of: BLE, WiFi, ATM, SS/7, X.25, WiMAX, SCCP, DUP, B-ISUP, ISUP, TUP, TCAP, SSCOP, H.323, SIP, BICC, IS-41, IS-634, CAS, CS1, CS2, R2, CAMEL, INAP, MAP.

In some embodiments, digital filters are an equalizer with a frequency band control step of 50 Hz, as well as with the ability to control the volume and level of the audio signal.

In some embodiments, digital filters can be configured by a physician on his own based on his individual psychoacoustic characteristics, or selected by the physician from the preset settings.

In some embodiments, information about the patient can be selected from a group consisting of: full unique name, age, sex, contact details, medical record number, video recording of a telemedicine consultation, full name of the attending physician, etc.

In some embodiments, at least one digital filter is applied to the audio signal sequentially or simultaneously.

BRIEF DESCRIPTION OF THE DRAWINGS

The attached drawings, which are included in this description, illustrate embodiments of the invention and serve to explain the principles of this invention together with the foregoing general description of the invention and the following detailed description of the embodiments.

FIG. 7 demonstrates the operation of the claimed invention in the physician-patient mode on the physician's smartphone.

DETAILED DESCRIPTION OF THE INVENTION

In general, the present invention is aimed at creating a simple and universal digital stethoscope, the use of which makes it possible for a physician to perform auscultation both during a personal examination and during a real-time telemedicine consultation using the same device. Moreover, in emergency cases, the digital stethoscope can be used by the patient himself. The claimed digital stethoscope is designed for auscultation of the heart, lungs, large vessels, bowels, as well as fetal heartbeat during pregnancy after 30 weeks of pregnancy. It is possible to use a stethoscope in veterinary practice.

A digital stethoscope is a complex of software and hardware that includes the following:

hardware, which is a device for detecting analog acoustic signals from the human body and generating digital signals based on detected acoustic signals; and software executed in the form of a PWA (progressive web application) built on open free technologies and protocols (JavaScript, HTML5, SSL, CSS3, Web Bluetooth API, Web Audio API, WebRTC Peer-to-peer connections).

The software is platform-independent and works on a smartphone, a personal computer (hereinafter referred to as a PC), a tablet via the web application interface. Modern computers and smartphones have great computing capabilities that allow the software to process information at high speed and in real time, while maintaining the usual interface and operating modes. The security of personal data is ensured by encrypting the transmitted information.

In the proposed design of the digital stethoscope, the generation and digital filtering of the audio signal occurs not in the microcontroller of the device for detecting analog acoustic signals (hereinafter referred to as the stethoscope), but in the software installed (running) on the user's or physician's device (web application), which receives data packets from the stethoscope using the Web Audio API or any other communication network and generates the bite flow transformed into sound signals according to the application settings.

This significantly reduces the cost of a digital stethoscope and allows users to quickly supply new algorithms for generating and processing the resulting sound. Thanks to this, a standard smartphone, PC or tablet can be used for simultaneous connection of both a stethoscope and wireless and/or wired headphones, since the stethoscope is connected to a smartphone, PC or tablet via a wireless data channel, and not as a headset, for example, a Bluetooth headset. The Bluetooth channel (or any other wireless channel) remains free to connect the headset and the problem of simultaneous use of two Bluetooth devices with one claimed device is solved. The data packet from a stethoscope can simultaneously be transmitted via the Internet in real time to an unlimited number of smartphones, PCs or tablets and relayed into headphones connected to these portable computing devices.

Figure 1:
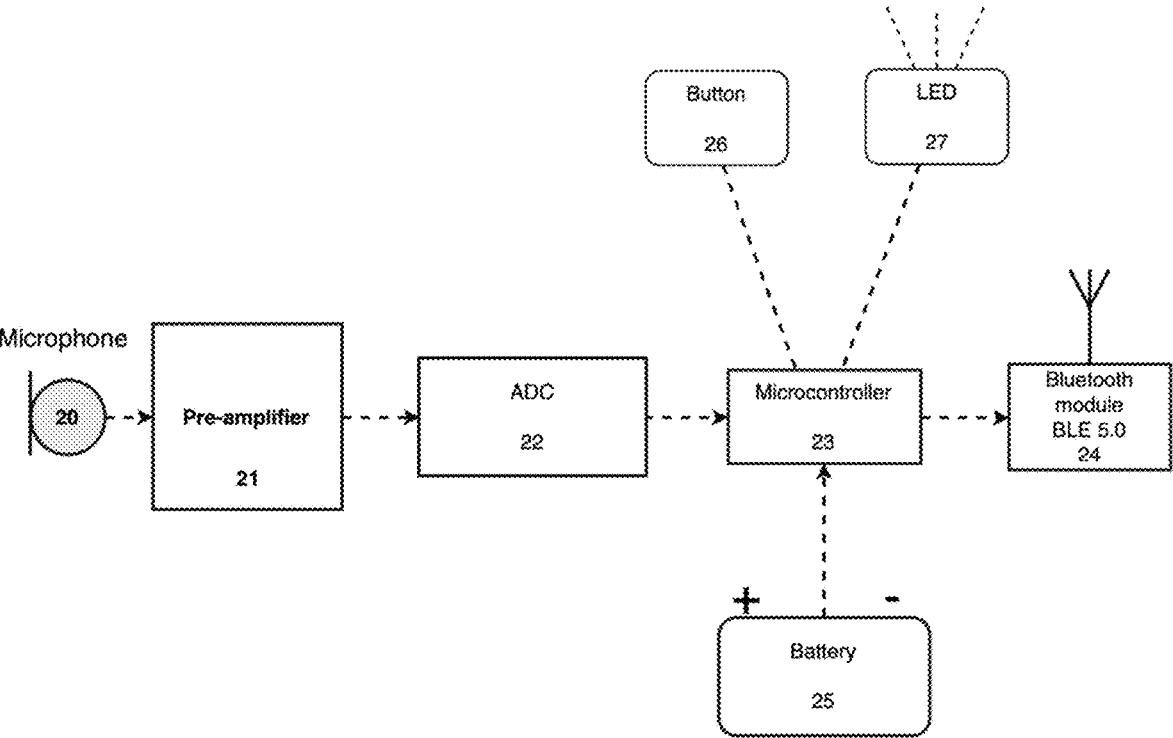
FIG. 1 demonstrates schematic representation of parts of the stethoscope.

FIG. 1 demonstrates a representation of a device "for detecting analog acoustic signals (stethoscope) from the human body", operating in accordance with the principles of the approximate embodiment of the present invention in the form of a hardware unit, functionality and data transmission. The stethoscope comprises a microphone 20 connected sequentially, an analog signal pre-amplifier 21, an ADC 22, a microcontroller 23 for combining signals from the ADC and signals about the status of the stethoscope (information about the battery charge 25 by means of an LED 27 and about the operating status of the device (turned on), information about the degree of signal amplification by means of an LED 27) into a single digital packet data and digital data transmission module 24, which is configured to transmit a single digital packet containing digital data to the information collection and processing system. In this case, the microcontroller 23 controls the signal LED 27 of the stethoscope to alert the user about the battery 25 charge level and about the operation mode of the analog signal preamplifier 21, as well as in the case of switching the stethoscope on and/or off.

In non-limiting embodiments, a single digital packet is transmitted according to the standard "BLE" (Bluetooth Low Energy) version 5.0 or later. A wireless channel for transmitting a digital packet can operate according to a standard selected from a group consisting of WiFi (e.g. IEEE Standard 802.11), ATM (Asynchronous Transfer Mode), SS/7 (Signaling System #7; e.g., ITU-T Recommendation Q.700), X.25 (e.g., ITU-T Recommendation X.25), WiMAX (Worldwide Interoperability for Microwave Access, e.g. IEEE Standards 802.16-802.16e), SCCP (Signalling Connection Control Part), DUP (Data User Part), B-ISUP (B-ISDN User Part), ISUP (ISDN User Part), TUP (Telephone User Part), TCAP (Transaction Capabilities Application Part), SSCOP (Service-Specific Connection Oriented Protocol), H.323, SIP (Session Initial Protocol), BICC (Bearer Independent Call Control protocol), IS-41, IS-634, CAS, CS1, CS2, R2, CAMEL (Customized Applications for Mobile network Enhanced Logic), INAP (Intelligent Network Application Part), MAP (Mobile Application Part).

All components of the device shown in FIG. 1 are assembled in a plastic case of original design. It should be noted that the device shown in FIG. 1 is not limited to any specific design or embodiment regarding its dimensions.

Figure 2:
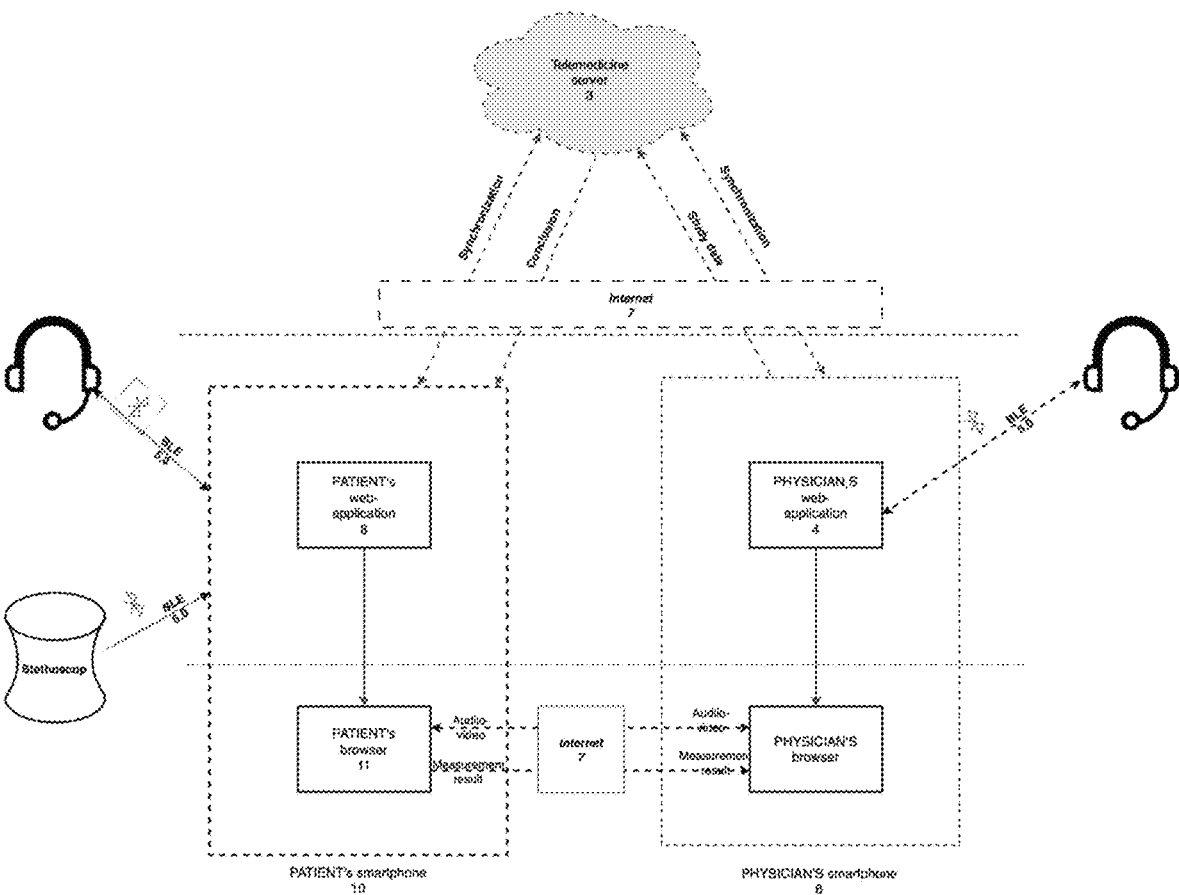
FIG. 2 demonstrates a digital signal processing algorithm for a real-time telemedicine consultation.
Figure 3:
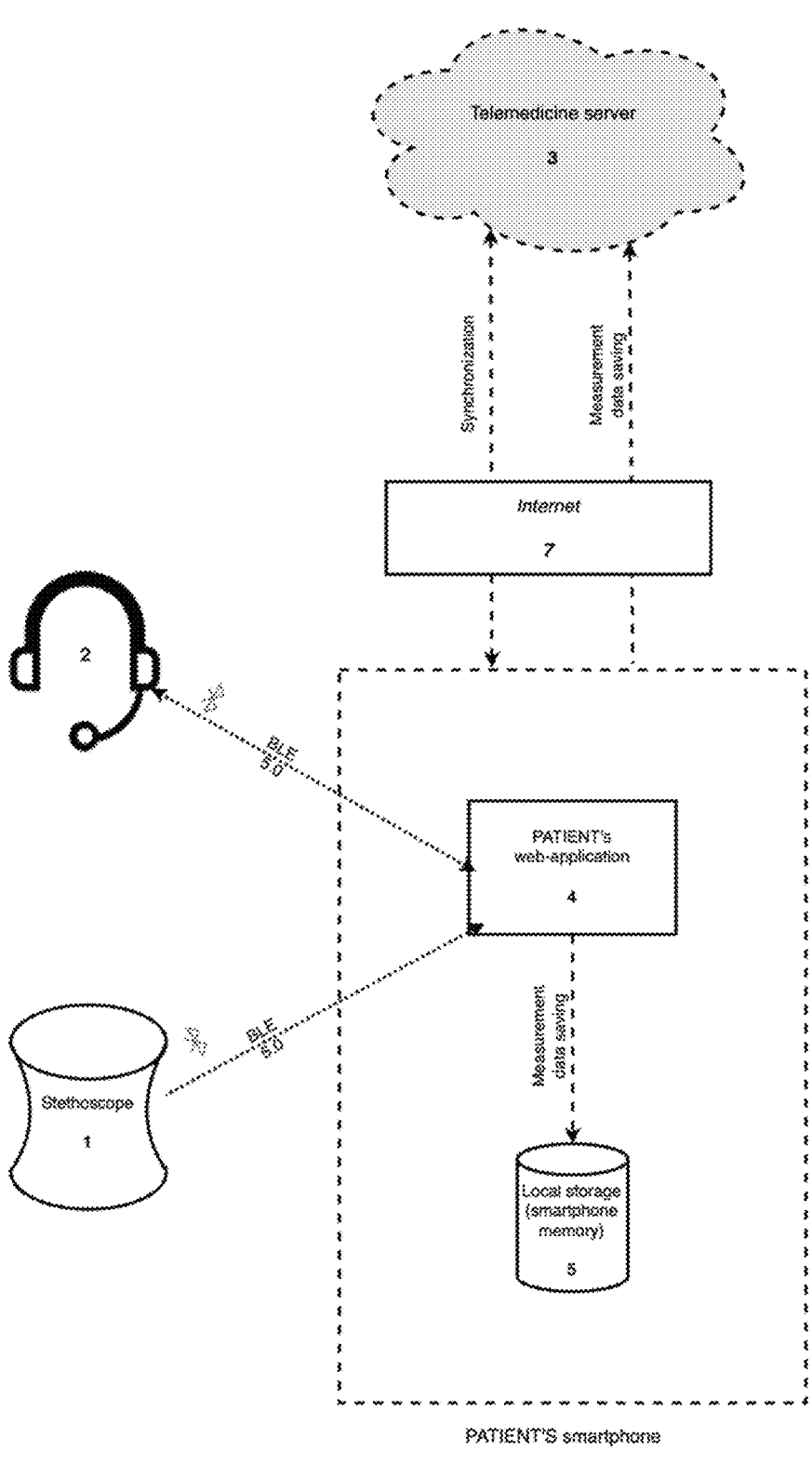
FIG. 3 demonstrates an operation scheme of the device in the physician-patient mode.
Figure 4:
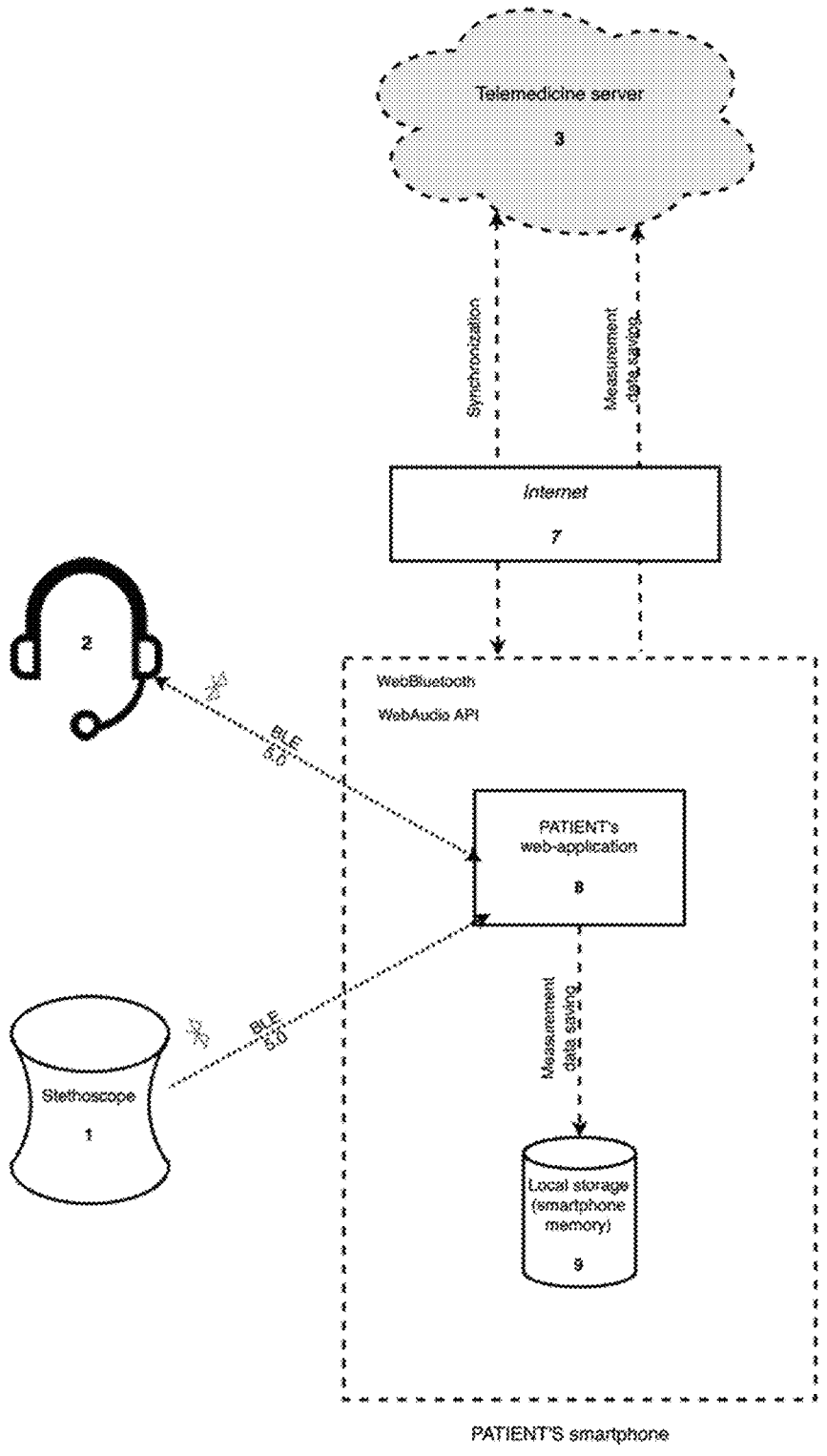
FIG. 4 demonstrates an operation scheme of the device in the self-use mode.

A flow chart of a digital stethoscope, demonstrating the approximate logical components of the nodes of the hardware and software parts of a digital stethoscope, in different operating modes of the same device, is shown in FIG. 2-4.

A digital data packet from the stethoscope 1 (a device for detecting acoustic signals) is transmitted to the data collection and processing system. The system for collecting and processing the received data from the stethoscope 1 is implemented through a secure encrypted web protocol and is accessible through the user interface of a progressive web application (PWA) configured to perform certain stages of signal processing and display.

The data collection and processing system is capable of working both locally, interacting with a stethoscope (self-use mode or "physician-patient" mode of operation in the format of in-person interaction, see FIG. 3, 4), or remote consultation ("telemedicine consultation" mode), see FIG. 2) obtaining digital packets via the WebRTC protocol from the user application to which the stethoscope is connected.

The user (patient or physician) starts a web application on his/her portable computing device in the web browser environment, after which the web application is connected to a stethoscope. Also, headphones are connected to the user's portable computing device. Packets with digital data from the stethoscope microcontroller 1 are transmitted using the digital data transfer module to the user's portable computing device (the physician's device 6 or the patient's device 10), where, by means of software algorithms, packets are parsed, including digital data, into service and useful information. The user's device might be a smartphone, a personal computer (PC), or a tablet.

The programming interface of a progressive web application (API) provides many interface calls through which the user can set rules. The digital stethoscope designed according to the present invention supports at least four user interfaces:

1. an interface for personal use that allows to listen, record and send the sounds of your heart or lungs to a physician or a neural network for analysis,
2. an interface for in-person auscultation that allows to listen, record in an electronic medical record, analyze and send the sounds of the patient's heart and lungs to the neural network for analysis,
3. patient interface for telemedicine consultation, allowing to select a physician and contact/her for a telemedicine consultation using a stethoscope,
4. physician interface for telemedicine consultation, in which the physician remotely controls the patient's stethoscope, sees the patient's actions, selects the mode and digital filters and hears the sound in real time, and can also issue conclusions both on previously recorded sounds and on the sounds that the physician hears during the telemedicine consultation. Later, the physician will be able to use online assistants based on artificial intelligence to analyze sounds, for example, to compare recordings in real time.

Digital data packets received from a stethoscope contain useful and service information. Service information (battery charge, preamp operation mode) is displayed in the user interface of a progressive web application opened in the web browser of the user's device, while the useful information is processed by the sequence of operations of the application subroutine according to the present invention and is combined into a byte stream, from which an audio signal is generated, which is subjected to noise reduction using noise reduction software packets, software application of digital filters. The audio signal obtained as a result of such processing is transmitted to the headphones 2, 14 of the physician or patient and displayed on the screen of the user's device in the form of an audiogram (phonocardiogram) in real time. FIG. 2-4 demonstrates an unlimiting example of the use of wireless headphones, however, it should be borne in mind that this invention allows using both wire and wireless headphones. The claimed invention can also be used simultaneously with several headphones, smartphones, personal computers, or tablets.

Sound records, user personal data and personal settings, as well as a physician's opinion on the results of auscultation are stored in data storages. The data storage can be cloud-based and/or local. The data storage can be public and/or private and/or hybrid.

FIG. 2-4 shows the use of a local data storage 5, 9 on the user's device. The local data storage 5,9 can be copied to the remote telemedicine web server 3 to ensure synchronization between portable computing devices of the patient and/or the physician via the Internet, providing access to physicians or neural networks for retrospective analysis of stored records, as well as for training a neural network that can be used by a physician as an online assistant during the auscultation.

This online assistant can give the physician a signal about possible health problems in the examined patient based on the analysis of the sound received, taking into account the presence of other previously recorded sounds of the functioning of the organ examined. The assistant is updated automatically when the user device is connected to the Internet. If necessary, the physician can enable an online assistant working on the basis of a neural network directly on the user's device.

Thus, signal processing and accumulation takes place on the user's portable computing device, while the user's portable computing device synchronizes the available data with a telemedicine web server, which is used for backup data storage, as well as for training a neural network. Synchronization is carried out via the Internet 7 (Internet Protocol, IP).

The term "web browser" implies a reference to any software application or combination of software/hardware that can act as a user agent, extract resources using communication protocols and display, representation or display of the data that have been extracted. The term "browser window" mainly refers to the actual window of the screen, that is, to the area in which the contents is displayed. Unless otherwise specified, the term "browser window" does not imply a reference to a window object managed by the window administrator.

The term "progressive web application" (PWA) in this context is intended to describe technologies in web development that visually and functionally transform a website into an application (a mobile application in a web browser). PWA is a hybrid solution and allows opening the application using a mobile browser. The same PWA can be run on a computer, or smartphone, or tablet with different operating systems (iOS, Android, Windows, Unix, etc.), which significantly reduces the cost of developing and maintaining a web application, as well as being installed for access in isolated local networks with increased security requirements. The functionality of the native application is fully preserved: sending push notifications; working offline; access to the hardware of the device (with restrictions); installing a shortcut (icon) on the desktop of the user's device, which visually does not differ from the shortcut of the native application. According to the invention, websites are considered as applications or web applications.

In the telemedicine consultation mode (FIG. 2), the patient's local web browser establishes a connection with the web browser installed on the physician's device using the WebRTC protocol. Within this connection, browsers can exchange a stream of audio, video data and content in real time without installing plugins or other extensions.

Through the digital data channel, the patient's web browser 11 transmits diagnostic information in the form of a byte stream received from the stethoscope 1. The physician's web browser 12, having received a byte stream from the patient, directs them to software that redirects the byte stream via the WebRTC protocol to the WebAudio API of the web browser installed on the physician's device for synthesizing the audio signal received from the patient's stethoscope 1. Further operation with the audio signal is similar to the operation in the self-use mode and/or the physician/patient mode (in-person consultation). The audio signal obtained as a result of the processing is transmitted to the headphones 2, and at the same time to the headphones 1 of the physician 2, 14 or patient and displayed on the screen of the user's device in the form of an audiogram (phono-cardiogram) in real time.

Figure 5:
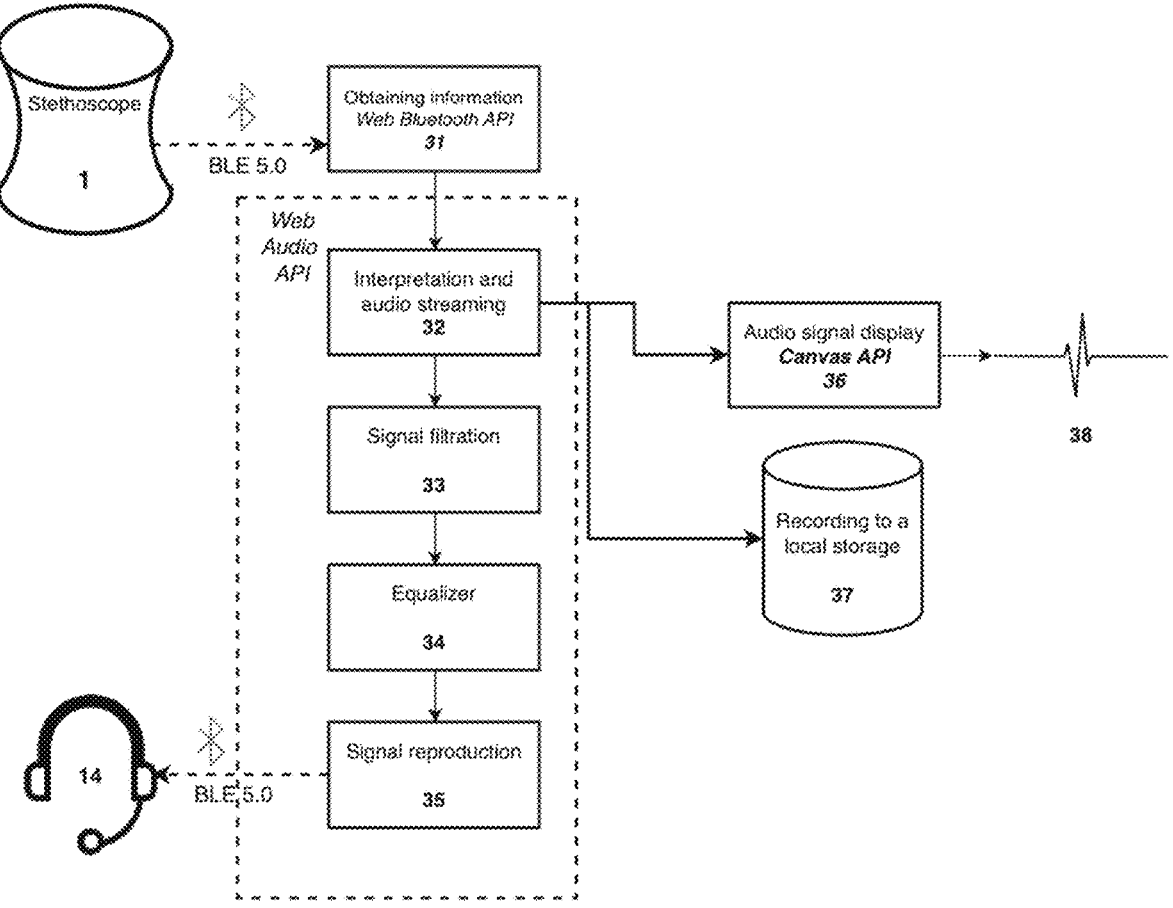
FIG. 5 demonstrates an operation scheme of the device in the telemedicine consultation mode.

FIG. 5 demonstrates a detailed flow chart of the digital stethoscope for in-person auscultation in the patient-physi-cian scheme (in-person auscultation) or in the self-use mode, illustrating the processing of the data packet received from the stethoscope 1.

The patient or physician connects the stethoscope 1 and at least one pair of headphones 14 to play the audio signal to the user's portable computing device, for example, to a smartphone, or a user computer, or a tablet, via a selected wireless data transmission channel, for example, via the Bluetooth channel. The web application is started on the user's (physician's or patient's) device in the web browser environment. The web application is connected to the stetho-scope 1 via the Web Bluetooth API (step 31).

The web browser is configured in such a way as to be able to switch between the following modes: the data entry mode, in which fields for data entry appear in the open browser window; auscultation modes, a mode for selecting various options and equalizer settings, a mode for saving notes about the performed auscultation The user interface of the web application in data entry mode is configured to accept data input from the user (either a physician or a patient). Depending on the mode of the device use, the patient or the physician enters the patient's data, which are stored in the data storage of the user's device and which is assigned a unique identifier (User ID), for example, based on random numbers, or by using a hash function from its data. The web application adds an entry about a new user to the list of users that can be stored in the data storage. The user record may contain the following data: unique identifier (User ID), information about the full (unique) name of the patient, his/her age, sex, contact details, etc., without any limitations.

In the case of self-use, the patient, after entering his/her data, begins auscultation according to the instructions attached to the stethoscope. The instructions describe the points for the heart and lung auscultation. In the case of an in-person consultation, the physician, having entered the data, begins the auscultation. In the case of repeated use of the digital stethoscope, the physician selects the patient from the list of users and starts the auscultation mode.

The sound passing through the membrane of the stetho-scope 1 is captured by an audio microphone. Next, the signal passes through the amplifier, is converted into digital form, enters the microcontroller, and using a wireless data trans-mission channel, the digital data flow is sent to the WebAu-dio API of the web browser installed on the user's device (physician's or patient's) to process the received digital data flow to synthesize the audio signal from the received digital data packet.

The next step: the user switches the user interface to the sound recording mode. The software generates sound from the received byte stream at frequencies of 20-3000 Hz—stage 32, at which the interpretation and audio streaming takes place. The received audio signal is analyzed by soft-ware algorithms for the signal-to-noise ratio. Based on the algorithm, the web application distinguishes the level of the incoming signal and gives the user a signal about insufficient signal quality if the received signal has an incorrect signalto-noise ratio. If the signal is of high quality (which is a psychoacoustic concept in which the physician clearly hears the necessary sounds of breathing or heartbeat, while he/she is not disturbed by background external noise), then the user (either a patient or a physician) turns on sound recording, which is stored locally in data storage 37 on the user's portable computing device, and can also be sent to a telemedicine server via the Internet for retrospective analy-sis by the physician or a neural network. After recording the audio signal and saving it to the data storage, the user interface mode switches to the display mode, on which the audio signal is displayed via the Canvas API (step 36). The sound is played in the web browser window as an audiogram (phonocardiogram).

The next step (step 33 and step 34): the software generates and applies digital filters selected by the physician to the audio signal received at the previous step: the audio fre-quency range necessary for listening to the heart or lungs is allocated using the software. Digital filters are an equalizer with a frequency band control step of 50 Hz, as well as with the ability to control the volume and level of the audio signal. The physician is given the opportunity to set up his own digital filters based on his/her experience and his individual psychoacoustic characteristics, or use preset set-tings created on the basis of scientific data on the sound frequency characteristics of the heart valves and breath sounds (see Table 1, Table 2). In the process of applying digital filters, it is possible to apply one or more filters at the same time.

TABLE 1

Frequency ranges of the main auscultative signs of cardiac activity used for digital filter pre-setting

| Sign | General frequency range, Hz | Typical frequency range, Hz |
| --- | --- | --- |
| Normal first sound | 20-1400 | 90-180 |
| Muffled first sound | 20-710 | 45-90 |
| Snapping first sound | 20-2800 | 180-355 |
| Normal second sound | 20-1400 | 90-180 |
| Metallic second sound | 45-1400 | 180-355 |
| Third sound (adventitious) | 20-1400 | 20-90 |
| The same for gallop rhythms | 20-1400 | 20-90 |
| Mitral valve opening snap | 20-5600 | 180-355 |
| Diastolic murmur of mitral stenosis | 45-1400 | 90-180 |
| Diastolic murmur of aortic regurgitation | 45-2800 | 355-710 |
| "Blowing" systolic murmur | 45-2800 | 180-710 |
| Pericardial friction rub | 90-2800 | 355-710 |

TABLE 2

Frequency ranges of the main auscultative signs of respiration used for digital filter pre-setting

| Sign | General frequency range, Hz | Typical frequency range, Hz |
| --- | --- | --- |
| Vesicular breath sounds | 45-2800 | 180-355 |
| Bronchial breath sounds | 45-2800 | 710-1400 |
| Bronchovesicular breath sounds | 45-2800 | 355-710 |
| Coarse crackles | 180-2800 | 180-360 |
| Intermediate crackles, low-pitched | 90-2800 | 180-355 |
| Intermediate crackles, high-pitched | 45-2800 | 355-710 |
| Fine crackles, low-pitched | 45-2800 | 180-355 |
| Fine crackles, high-pitched, crackling sound | 90-5600 | 710-1400 |
| Wheezes, buzzing | 45-1400 | 180-710 |

TABLE 2-continued

Frequency ranges of the main auscultative signs of
respiration used for digital filter pre-setting

| Sign | General frequency range, Hz | Typical frequency range, Hz |
|---|---|---|
| Wheezes, whistling | 90-2800 | 355-710 |
| Pleural rub | 90-2800 | 710-1400 |

Next step (stage 35) The resulting digital filtering sound is transmitted to the physician's headphones for the purpose of listening to it. During auscultation, the physician hears the sound and sees a graphical display of the sound on the screen (a phonocardiogram or the sound of breath sounds), which greatly facilitates diagnosis and allows real-time use of digital filters in the form of equalizer settings that change certain frequencies. If necessary, the physician can enable an online assistant working on the basis of a neural network directly on the user's device in real time.

The next step: the physician takes notes on the diagnosis made, selects the information to be uploaded to the data storage, confirms the download of this information and saves the patient's file. In some embodiments, the web application checks the names of downloaded files, with the names of files that are already in the storage list to identify possible collisions.

The record of the sound (stage 37) received from the stethoscope 1 into the data storage of the user's device takes place in WAV format, and the sound received from the stethoscope before the use of digital filters and information about the digital filters used, as well as about the diagnosis made by the physician and other data collected by the user interface (date and time, geolocation, sex, age of the patient, medical record number, video recording of a telemedicine consultation, etc.) is stored separately.

When the sound is saved on the user's device, the sound is synchronized and saved on a remote telemedicine web server to provide backup data storage, as well as automatic online training of a physician's assistant.

Figure 6:
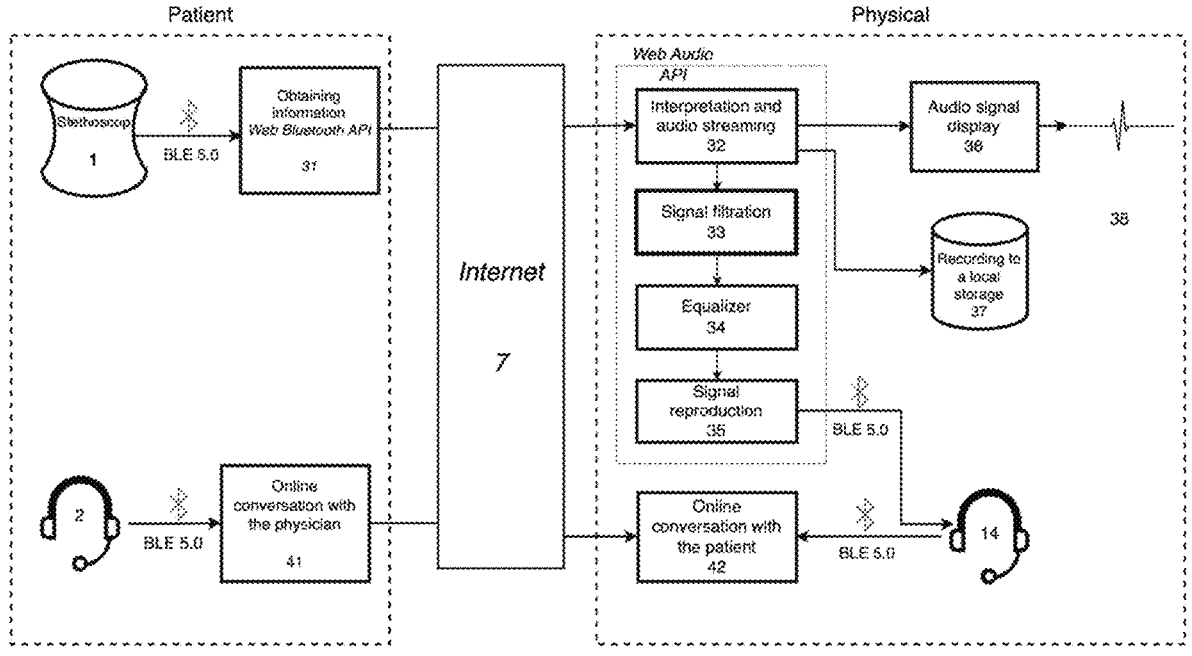
FIG. 6 demonstrates an operation schemed of the device in the in-person consultation mode.

FIG. 6 demonstrates a detailed flowchart of the digital stethoscope for auscultation in the telemedicine consultation mode.

The patient connects the stethoscope 1 and headphones 2 to the user's device, which can be selected from: a user computer, tablet, smartphone, and launches a progressive web application 8 on his device in a web browser 11, selecting a physician from the list of specialists who are ready to conduct a consultation, and sends a connection request to the physician via Internet 7. First, the patient enters all his/her data through the user interface in the same way as during an in-person consultation.

The physician on his/her user device with headphones 14 connected to it in the web browser 12 and web application 4 confirms the request and gets access to the patient's data, and the sound in the headphones 14 received from the stethoscope 1. The patient's local web browser establishes a connection with the web browser installed on the physician's device using the WebRTC protocol. Within the connection, the browsers may exchange audio, video and digital data.

According to the present invention, in the telemedicine consultation mode the verbal communication between the physician and the patient takes place via the audio data channel, video information is exchanged via the video data channel from the smartphone camera, or PC, or tablet of the physician and the patient—the physician and the patient see each other. Both verbal and visual contact is established (stage 41,42) between the patient and the physician. This solves the problem of controlling the patient's actions, which may arise when using a digital stethoscope by the patient independently. The physician sees that the sound is being recorded by the stethoscope 1 from that patient he is consulting, and it also makes it easier to receive a high-quality audio signal from the stethoscope, because the physician hears the sound from the stethoscope 1 in real time and can give guidance to the patient on placing the stethoscope in a particular position.

Through the digital data channel, the patient's web browser transmits diagnostic information in the form of a byte stream received from the stethoscope 1. The physician's web browser, having received a byte stream from the patient, directs them to the software, which redirects the byte stream to the Web Audio Api of the physician's browser, and the sound synthesis (stage 32) received from the patient's stethoscope takes place on the physician's device. Working with the audio signal is similar to operating during an in-person consultation. Digital filters are applied to the audio signal, including noise reduction algorithms (filtering and attenuation of diagnostically insignificant audio frequencies, instantaneous frequency cutting based on signal analysis using Fast Fourier transform). The physician can select digital filters, as well as control the volume and signal level (steps 33-34).

If necessary, the physician in the software can include a graphical display of the received sound wave in the form of a phonocardiogram (PCG) both in the entire spectrum of the received frequencies and at frequencies that better characterize the work of a particular organ or part of it (e.g., to highlight the main carrier frequency of the mitral valve functioning sound).

If necessary, the sound can be recorded in whole or in part with simultaneous storage of information locally in the data storage of the user's device with duplication of information to the telemedicine server (3) via the Internet (7), as well as issue a conclusion on the results of auscultation and enter it into the patient's electronic medical record. The recorded sound is stored without processing with digital filters before they are applied, so that the physician who will retrospectively analyze the sound is not limited in the use of digital filters and the sound is reproduced in full, with reference to information about the digital filters applied by the physician and the equalizer settings.

Sound playback (stage 35) is carried out through the headphones of the physician 14. In some embodiments of the invention, the sound transmitted to the physician's headphones 14 via the Internet can be relayed to a remote smartphone, or PC, or tablet for analysis by another physician or artificial intelligence. The sound of interest for the physician can be recorded and re-analyzed by another physician or used for comparative analysis during subsequent auscultations.

In some embodiments, the physician can enable real-time audio analysis using a neural network running in a web application.

The main advantage of the digital stethoscope being developed is that its division into hardware and software parts allows easily updating and upgrading the algorithms used for audio signal processing, as well as configure them in real time for each particular physician and patient, using the computing power of a smartphone, PC or tablet. Sound processing and digital filtering takes place on the user's device using software algorithms, and not in a stethoscope using a microprocessor or bandpass filters based on transistors. The use of wireless headphones allows safe auscultation of patients with highly contagious diseases.

Example 1

Figure 7A:
FIG. 7A demonstrates the initial screen of the application with the patient's data (on the left) and the start screen of the auscultation showing the dashboard and the auscultation mode selection elements (on the right).
Figure 7A:
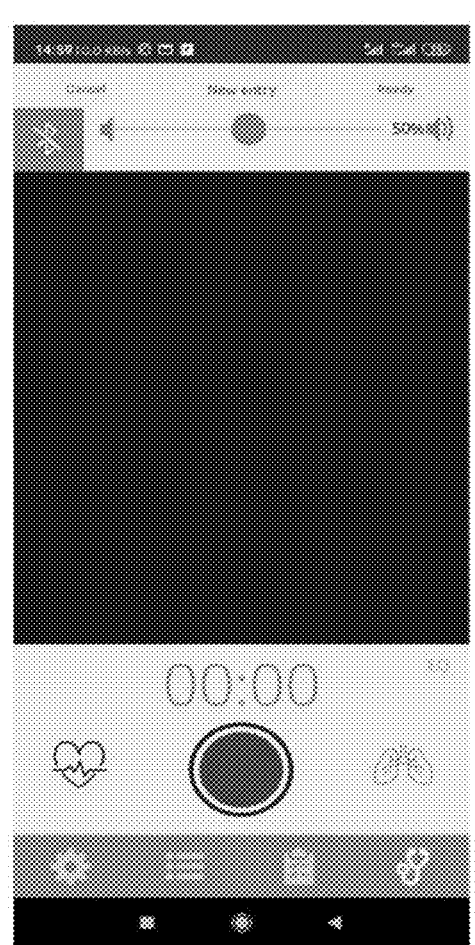
Figure 7B:
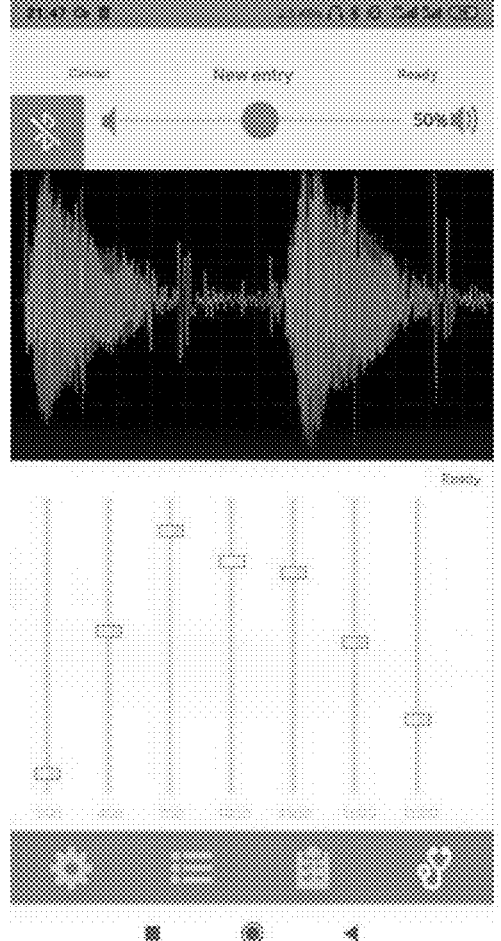
FIG. 7B demonstrates the auscultation screen with the use of an equalizer, which shows a graphical representation of the auscultation result in real time of the patient (on the left), and the application screen with the final stage of the applied algorithm, which shows a window with the possibility of saving the audio signal and the possibility of filling in the field with a medical conclusion.
Figure 7B:
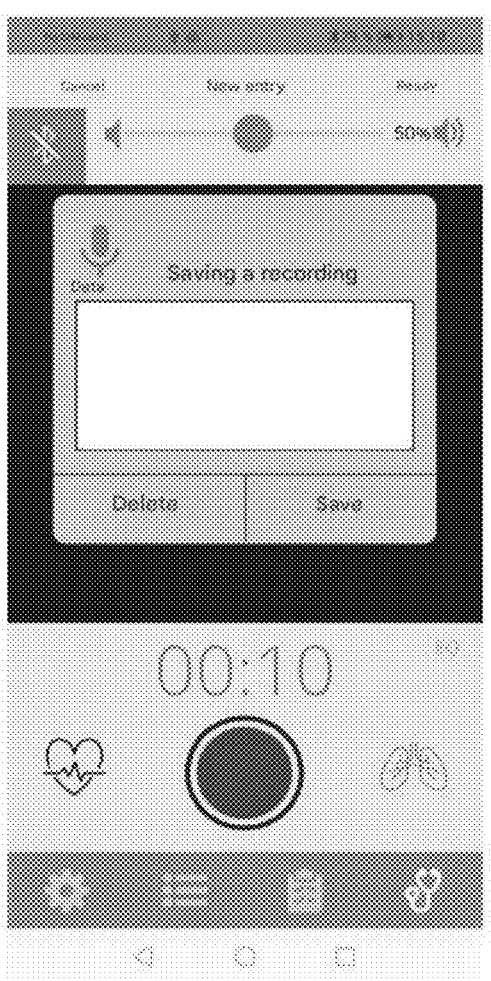

A female patient aged 45 years with an early-stage aortic valve insufficiency, and stage 3 obesity. Typical auscultation at the apex of the heart (auscultation point of the aortic valve) in this patient is extremely difficult due to the pronounced subcutaneous fat tissue, as well as large breasts. The physician used the developed digital stethoscope in the "patient-physician" mode in the +40 dB gain mode with an equalizer accentuation at frequencies of 300-700 Hz (the total gain of the required frequencies was +60 DB, which approximately corresponds to a 1000-fold increase in volume). The parameters were selected in the application on the physician's smartphone. For this purpose, the file with the patient's data (FIG. 7A) was created, containing an audio signal record and the results of its software based processing performed using the selected parameters. A diastolic murmur was detected, which is also visible in the graphical representation of the real-time auscultation finding (see FIG. 7B). After that, the physician saves his/her medical conclusion. The diagnosis of an aortic valve defect was made based on auscultation findings.

Example 2

Another electronic stethoscope was used on the same 45-year-old patient. The sound amplification in this stethoscope was the most pronounced (a 24-fold increase). Due to the pronounced fat tissue and large-sized breasts, the physician was not satisfied with the sound amplification at the aortic valve projection point that was available. At the same time, it was also not possible to accentuate the equalizer at frequencies of 300-700 Hz and visualization of the resulting sound was not available. Together, this led to an 8-old increase in the duration of the auscultation itself and required additional verification of the diagnosis using other examinations.

The physician noted that in that situation, when there was only an early-stage defect, it was possible to easily and concomitant factors in the form of obesity, it is easy to miss the defect during auscultation with stethoscopes available on the market. Diagnosis in such cases is made much later as symptoms worsen and with the use of additional examination methods.

Thus, based on the presented examples 1 and example 2, it can be seen that the developed digital stethoscope processes the audio signal with high quality, processing speed, enabling the physician to interpret the audio signal with the possibility of adapting its processing to their individual characteristics in order to make an accurate diagnosis in real time.

The use of large sound amplification due to the ability to apply digital amplification, the possibility of online sound analysis using neural networks gives an additional advantage to physicians in the speed of diagnosis and reduces the requirements for healthcare personnel to have sufficient experience in auscultation-based detection of heart and lung diseases.

As used in the description and claims of this invention, the terms "includes" and "including" are interpreted as meaning "includes but not limited to". These terms are not intended to be interpreted as "consists only of".

Although the invention has been described with reference to the disclosed embodiments, it must be apparent to those skilled in the art that the specific embodiments described in detail are for illustrative purposes only and should not be construed as limiting the scope of the invention in any way. It should be appreciated that various embodiments understandable for those skilled in the art are possible without departing from the essence of the present invention.

The invention claimed is:

1. A digital stethoscope comprising:
   a device for detecting analog acoustic signals from a patient and at least one data processing system implemented via a secure encrypted web-protocol and accessible via a user interface of a progressive web-application on at least one portable computing device of a patient and/or physician with at least one pair of connected headphones;
   wherein the device for detecting analog acoustic signals from the patient comprises a sequentially connected audio microphone, an analog signal pre-amplifier, an ADC, a microcontroller, a battery; the microcontroller is configured to combine signals from the ADC and signals about a status of the device into a single digital packet and transmit the digital packet containing digital data via a wireless data transmission channel to the at least one data processing system,
   and at least one data processing system is configured to receive the digital packet and its software processing in real time in a progressive web application running on the device of the physician and/or patient, wherein the user interface of the progressive web application provides a variety of interface calls selected from a group consisting of: an interface for personal use, an interface for in-person auscultation, a patient interface for telemedicine consultation, a physician interface for telemedicine consultation, and the progressive web application configured to execute the following commands:
   obtaining patient information and storing data in a data storage;
   processing of the digital packet with subsequent conversion of data from the digital packet into an audio signal and into device status data for detecting the analog acoustic signals,
   saving device status data and the audio signal to the data storage,
   displaying the audio signal in real time as an audiogram in a web browser window of the physician,
   processing of the audio signal based on user settings, including applying software noise reduction algorithms to the audio signal and applying at least one digital filter on the audio signal,
   output of the processed audio signal in real time via an audio channel of the patient's and/or physician's portable computing device to at least one pair of headphones, and
   storing data on applied digital filters to the audio signal and data on analysis performed by a physician and/or a neural network in the data storage.

2. The digital stethoscope according to claim 1 wherein the device for detecting analog acoustic signals from a patient additionally comprises at least one LED and an element to turn on/off the device that is connected to a microcontroller, wherein the microcontroller is configured to supply a control signal to at least one LED to turn it on in the event of a decrease in battery charge and/or in the case of switching the device on and/or off.

3. The digital stethoscope according to claim 2, wherein the signals about the status of the device are the signals selected from a group consisting of: information about the battery charge, information about turning on the device, and information about the degree of amplification of the analog signal received from the analog signal pre-amplifier.

4. The digital stethoscope according to claim 1 wherein, when used for a telemedicine consultation, it includes two portable computing devices, one of which belongs to the patient, and the other one to the physician, wherein the data processing system, accessible through the user interface of a progressive web application in a web browser on the patient's portable computing device is configured to receive a digital data packet from the device for detecting analog acoustic signals via a telecommunications channel, while the data processing system accessible through the user interface of a progressive web application in a web browser on the physician's portable computing device is configured to receive a digital data packet from the patient's data processing system and its software processing in real time.

5. The digital stethoscope according to claim 4 wherein the connection between the patient's web browser and the physician's web browser is established via a WebRTC protocol, within which the browsers exchange audio, video and digital data.

6. The digital stethoscope according to claim 1 wherein the user interface of a progressive web application is configured to allow the user to select modes selected from a group consisting of: a mode for receiving input from a patient or a physician, an audio recording mode, an audio display mode in the form of an audiogram and applying at least one digital filter to it, a recording mode for analyzing the processed audio signal.

7. The digital stethoscope according to claim 1, wherein at least one portable computing device of the physician and/or patient is selected from a group consisting of: smartphone, personal computer, and tablet.

8. The digital stethoscope according to claim 1, wherein the data storage can be cloud-based and/or local.

9. The digital stethoscope according to claim 1, wherein the data storage can be public and/or private and/or hybrid.

10. The digital stethoscope according to claim 1, wherein the data storage is configured to be copied to a remote telemedicine web server to ensure synchronization between portable computing devices of the patient and/or the physician via the Internet, providing access to physicians or neural networks for retrospective analysis of stored records, and for training a neural network that can be used by a physician as an online assistant during auscultation.

11. The digital stethoscope according to claim 1, wherein the wireless channel for transmitting a digital data packet operates according to a standard from a group consisting of: BLE, WiFi, ATM, SS/7, X.25, WiMAX, SCCP, DUP, B-ISUP, ISUP, TUP, TCAP, SSCOP, H.323, SIP, BICC, IS-41, IS-634, CAS, CS1, CS2, R2, CAMEL, INAP, and MAP.

12. The digital stethoscope according to claim 1, wherein the digital filters are an equalizer with a frequency band control step of 50 Hz, and an ability to control the volume and level of the audio signal.

13. The digital stethoscope according to claim 12 wherein digital filters can be configured by a physician based on his individual psychoacoustic characteristics, or selected by the physician from at least one preset setting.

14. The digital stethoscope according to claim 1, wherein information about the patient can be selected from a group consisting of: full unique name, age, sex, contact details, medical record number, video recording of a telemedicine consultation, and full name of the attending physician.

15. The digital stethoscope according to claim 1, wherein at least one digital filter is applied to the audio signal sequentially or simultaneously.

\* \* \* \* \*